United States Patent [19]
Van Antwerp et al.

[11] Patent Number: 5,786,439
[45] Date of Patent: Jul. 28, 1998

[54] HYDROPHILIC, SWELLABLE COATINGS FOR BIOSENSORS

[75] Inventors: William Peter Van Antwerp, Valencia; Christian C. Decker, Beverly Hills; John J. Mastrototaro, Los Angeles, all of Calif.

[73] Assignee: MiniMed Inc., Sylmar, Calif.

[21] Appl. No.: 749,754

[22] Filed: Oct. 24, 1996

[51] Int. Cl.$^6$ .............................. C08G 18/72; B05D 3/00
[52] U.S. Cl. .................... 528/77; 427/2.12; 427/58; 428/423.1; 528/85
[58] Field of Search .................. 528/77, 85; 428/423.1; 427/2.12, 58

[56] References Cited

U.S. PATENT DOCUMENTS 5,614,586   3/1997   Tang et al. .
5,674,275   10/1997  Tang et al. .

FOREIGN PATENT DOCUMENTS

0624612A1   11/1994   European Pat. Off. .

*Primary Examiner*—John M. Cooney, Jr.
*Attorney, Agent, or Firm*—Townsend and Townsend and Crew LLP

[57] ABSTRACT

Methods for reducing the electrode impedance of implantable biosensors by coating the surface of the biosensor with a uniform hydrogel which allows unimpeded water movement around the sensor are provided. The surface coatings are compositions which are biocompatible and are capable of water uptake of at least 120% of their weight, more preferably at least 200% of their weight. Upon the uptake of water, the hydrogels used in the present invention will also swell and provide a layer of water around the electrodes to which the hydrogels are attached. The hydrogels can be prepared from (a) a diisocyanate, (b) a hydrophilic polymer which is a hydrophilic diol, a hydrophilic diamine, or a combination thereof, and optionally, (c) a chain extender.

15 Claims, 6 Drawing Sheets

 HEXAMETHYLENE DIISOCYANATE
+
 HYDROPHILIC DIOL
+
 CHAIN EXTENDER
↓
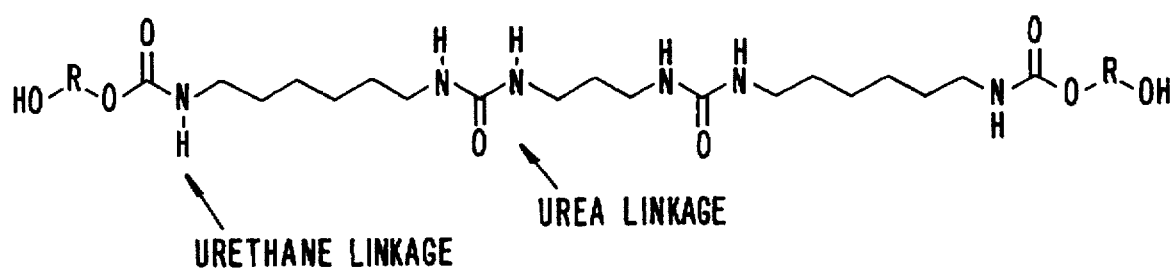
URETHANE LINKAGE     UREA LINKAGE
FIG. 1.

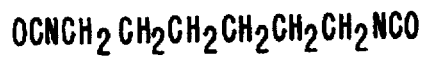 HEXAMETHYLENE DIISOCYANATE
HMI
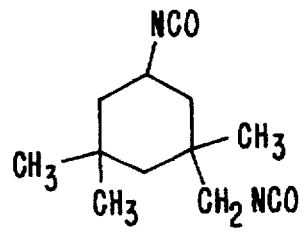 ISOPHORONE DIISOCYANATE
IPDI
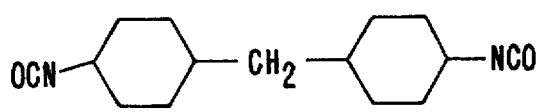 4,4'-DICYCLOHEXYLMETHANEDIISOCYANATE
H12MDI
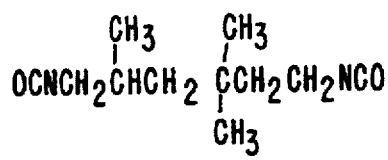 TRIMETHYLHEXAMETHYLENE DIISOCYANATE
TMDI
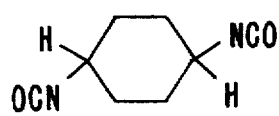 TRANS-1,4-CYCLOHEXANE DIISOCYANATE
CHDI
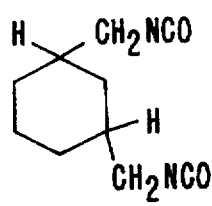 1,3-BIS(ISOCYANTOMETHYL)CYCLOHEXANE
CIS AND TRANS
*FIG. 2.*

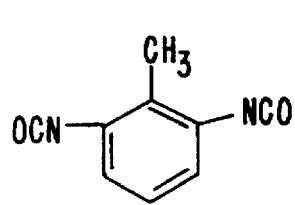 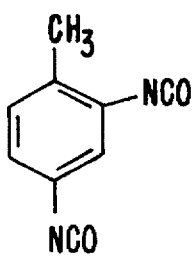 TOLUENEDIISOCYANATE TDI
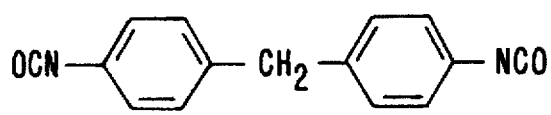 4,4'-DIPHENYLMETHANE DIISOCYANATE MDI
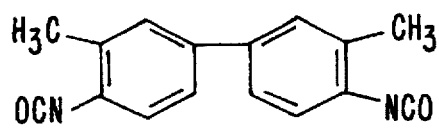 3,3'-DIMETHYL-4,4'-BIPHENYL DIISOCYANATE TODI
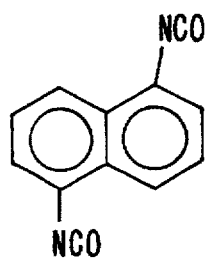 NAPHTAHALENE DIISOCYANATE NDI
 PARAPHENYLENE DIISOCYANATE PPDI
FIG. 3.

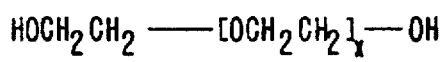 POLYETHYLENE GLYCOL
POLYETHYLENE OXIDE

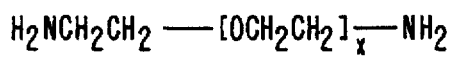 AMINE TERMINATED PEG
JEFFAMINE

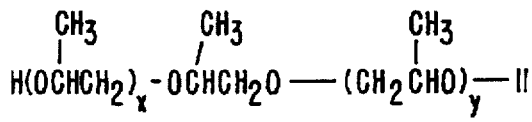 POLYPROPYLENE GLYCOL

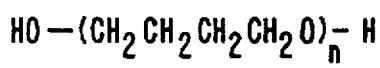 POLYTETRAMETHYLENE ETHER GLYCOL
PTMEG

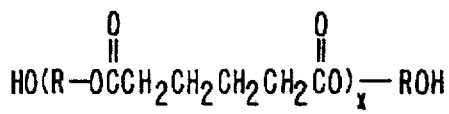 POLYESTER BASED POLYOL
R IS FROM:

—$CH_2CH_2$—  ETHYLENE GLYCOL

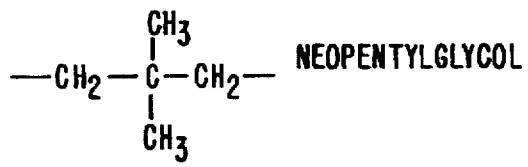 PROPYLENE GLYCOL

—$CH_2CH_2CH_2CH_2$—  1-4 BUTANEDIOL

NEOPENTYLGLYCOL

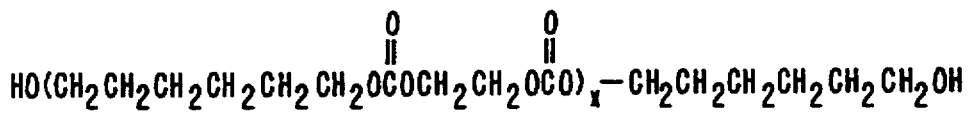
POLY 1-6 HEXYL, 1,2 ETHYL CARBONATE DIOL

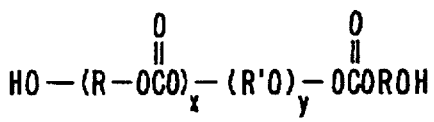 POLYCARBONATE POLYOL
R = ALIPHATIC, CYCLOALIPHATIC OR AROMATIC
R' = C2 TO C4 ALIPHATIC

FIG. 4.

| Structure | Name |
|---|---|
| HOCH₂CH₂OH | ETHYLENE GLYCOL |
| HOCH₂CH₂CH₂CH₂OH | 1,4-BUTANEDIOL |
| HO(CH₂)₆OH | 1,6-HEXANEDIOL |
| HOCH₂-cyclohexane-CH₂OH | 1,4-BIS(HYDROXYMETHYL)CYCLOHEXANE CIS AND TRANS |
| HOCH₂CH₂O-C₆H₄-OCH₂CH₂OH (para) | p-DI(2-HYDROXYETHOXY)BENZENE HQEE |
| HOCH₂CH₂O-C₆H₄-OCH₂CH₂OH (meta) | m-DI(2-HYDROXYETHOXY)BENZENE HER |
| H₂NCH₂CH₂NH₂ | ETHYLENEDIAMINE |
| diethyltoluene diamine structure | 2,4-DIAMINO-3,5 DIETHYLTOLUENE ETHACURE 100 2 ISOMERS |
| H₂N-C₆H₃(Cl)-CH₂-C₆H₃(Cl)-NH₂ | 3,3'-DIECHLORO-4,4'DIAMINODIPHENYL-METHANE MOCA |
| H₂N-C₆H₄-C(O)-O-CH₂CH₂CH₂-O-C(O)-C₆H₄-NH₂ | TRIMETHYLENE GLYCOL DI P-AMINO BENZOATE POLACURE 740 M |
| di(methylthio)toluene diamine structure | 2,4 DIAMINO 3,5 DI(METHLYTHIO)TOLUENE ETHACURE 300 |
| H₂N-C₆H₄-CH₂-C₆H₄-NH₂ | METHYLENEDIANILINE MDA |

*FIG. 5.*

HYDROPHILIC, SWELLABLE COATINGS FOR BIOSENSORS

RELATED APPLICATIONS

This application is related to U.S. Ser. No. 08/721,262, filed Sep. 26, 1996 which is a Continuation-in-Part of U.S. Ser. No. 08/410,775, which is now abandoned filed Mar. 27, 1995, the complete disclosures of each being incorporated herein by reference.

FIELD OF THE INVENTION

This invention lies in the field of polymer chemistry in which the polymers formed are suitable for coating biosensors. The coatings act to decrease the impedance at the sensor's electrode and thereby enhance the signal during in vivo placement of the sensor.

BACKGROUND OF THE INVENTION

Biosensors are small devices that use biological recognition properties for selective analysis of various analytes or biomolecules. Typically, the sensor will produce a signal that is quantitatively related to the concentration of the analyte. To achieve a quantitative signal, a recognition molecule or combination of molecules is often immobilized at a suitable transducer which converts the biological recognition event into a quantitative response.

A variety of biosensors have been developed for use with numerous analytes. Electroenzymatic biosensors use enzymes to convert a concentration of analyte to an electrical signal. Immunological biosensors rely on molecular recognition of an analyte by, for example, antibodies. Chemoreceptor biosensors use chemoreceptor arrays such as those of the olfactory system or nerve fibers from the antennules of the blue crab *Callinectes sapidus* to detect the presence of amino acids in concentrations as low as $10^{-9}M$. For a review of some of the operating principles of biosensors, see Bergveld, et al., ADVANCES IN BIOSENSORS, Supplement 1, p. 31–91, Turner ed., and Collison, et al., *Anal. Chem.* 62:425–437 (1990).

Regardless of the type of biosensor, each must possess certain properties to function in vivo and provide an adequate signal. First, the elements of the biosensor must be compatible with the tissue to which it is attached and be adequately shielded from adjacent tissues such that allergic or toxic effects are not exerted. Further, the sensor should be shielded from the environment to control drift in the generated signal. Finally, the sensor should accurately measure the analyte in the presence of proteins, electrolytes and medications which may interfere.

One of the problems with implantable biosensors occurs as a result of "road block" type interference. This problem is encountered when the outermost layer of the biosensor has some hydrophobic characteristics. These characteristics result in the accumulation of plasma proteins on the surface of the electrode after only short periods of direct contact with body fluids. The hydrophobic regions of the sensor surface are believed to denature the proteins resulting in large deposits of protein mass. The deposits then affect the sensor's performance through a physical interference in a "road block" type of effect. The protein deposition is a gradual process which creates a non-uniform, non-predictable diffusion path for the analyte to the sensor. Moreover, the effect on the sensor is a cascading type in which the protein deposits dissapate the normal voltages applied to the electrodes (i.e., the deposits increase the capacitance of the system). The resultant requirement for higher voltages to offset the increased capacitance increases the noise, ultimately compromising the validity of the sensor's output.

Other problems are also associated with implantable sensors having hydrophobic regions at the sensor's surface. In particular, subcutaneous tissue contains substantial amounts of lipid vesicles. By implanting a biosensor directly into tissue, a portion of the sensor may be implanted directly into, or flush against a very hydrophobic lipid region. This also limits the aqueous environment which is required around the sensor's electrodes.

What is needed in the art are new coatings for implantable sensors which are extremely hydrophilic and provide a substantial and uniform aqueous flow around the sensors. Quite surprisingly, the present invention provides such coatings and sensors equipped with those coatings.

SUMMARY OF THE INVENTION

The present invention provides methods for reducing the electrode impedance of implantable biosensors by coating the surface of the biosensor with a uniform hydrogel which allows unimpeded water movement around the sensor. The surface coatings are compositions which are biocompatible and are capable of water uptake of at least 120% of their weight, more preferably at least 200% of their weight. Upon the uptake of water, the hydrogels used in the present invention will also swell and provide a layer of water around the electrodes to which the hydrogels are attached.

In one group of embodiments, the hydrogels can be prepared from:

(a) a diisocyanate, (b) a hydrophilic polymer which is a hydrophilic diol, a hydrophilic diamine, or a combination thereof, and optionally, (c) a chain extender.

The present invention further provides implantable biosensors for measuring a variety of analytes, the biosensor having a coating as described above.

BRIEF DESCRIPTION OF THE DRAWINGS

FIG. 1 illustrates polymerization reactions of a diisocyanate with a poly(alkylene) glycol or a diamino poly (alkylene oxide) which results in a polyurethane or polyurea, respectively.

FIGS. 2 and 3 provide the structures of certain aliphatic and aromatic diisocyanates which are useful in forming the coatings described below.

FIG. 4 provides the structures of a number of hydrophilic polymers including poly(alkylene) glycols and diamino poly (alkylene oxides) which are used in polymers described below.

FIG. 5 provides the structures of some chain extenders which are useful in the present compositions. This include aliphatic diols, diamines and alkanolamines and further include some aromatic diols and diamines.

FIG. 6 illustrates portions of a glucose sensor which can be coated with a hydrophilic swellable coating of the present invention.

DETAILED DESCRIPTION OF THE INVENTION

Figure 6A:
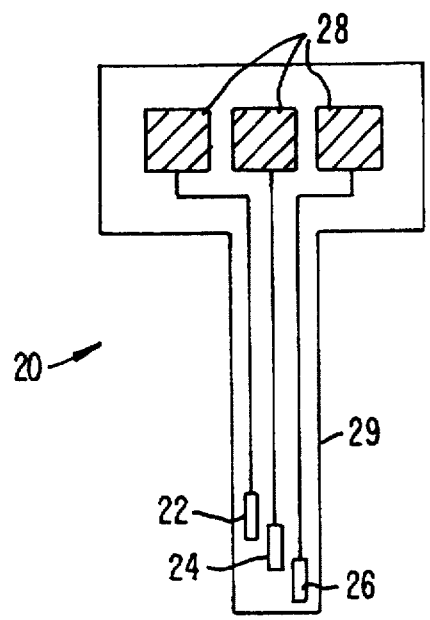
FIG. 6A is a schematic top view of a glucose sensor having electrodes covered with a polymer composition of the invention.

The following abbreviations are used herein: dl, deciliter; DEG, diethylene glycol; DMF, dimethyl formamide; PBS, phosphate buffered saline; THF, tetrahydrofuran; DI, deionized; PEG, poly(ethylene)glycol; mv, millivolts.

As used herein, the term "polyurethane/polyurea" refers to a polymer containing urethane linkages, urea linkages or combinations thereof. Typically, such polymers are formed by combining diisocyanates with alcohols and/or amines. For example, combining isophorone diisocyanate with PEG 600 and 1,4-diaminobutane under polymerizing conditions provides a polyurethane/polyurea composition having both urethane (carbamate) linkages and urea linkages (see FIG. 1).

Methods for Reducing Electrode Impedance of Biosensors

In one aspect, the present invention provides methods for reducing electrode impedance of biosensors by coating the biosensor with an extremely hydrophilic polymer such as a hydrogel or a cellulose acetate. Typically, the polymer is applied to the surface of the sensor by spin coating, dipping or spraying. Methods of spraying including traditional methods as well as microdeposition techniques with an inkjet type of dispenser. Additionally, the polymer can be deposited on a sensor using photo-patterning to place the polymer on only specific portions of the sensor. This coating of the sensor provides a uniform water layer around the sensor which allows for improved diffusion of various analytes to the sensor.

A hydrogel is a highly-interdependent, biphasic matrix consisting of a solid component (usually a polymer, and more commonly a highly cross-linked polymer) that has both hydrophilic and hydrophobic character. Additionally, the matrix has a liquid component (e.g., water) that is retained in the matrix by intermolecular forces. The hydrophobic character provides the matrix with a degree of water insolubility while the hydrophilic character affords water permeability.

The polymer portion of the hydrogel will contain functionality which is suitable for hydrogen bonding (e.g., hydroxyl groups, amino groups, ether linkages, carboxylic acids and esters, and the like). Moreover, the affinity for water presented by the hydrogen bonding functionality must be of sufficient degree that the hydrated hydrogel will retain the water within its matrix even upon placement of the hydrogel in a hydrophobic medium such as an oil or lipid matrix. In addition to this binding of water within the hydrogel matrix, the hydrogel should allow water to flow through it when placed in an aqueous environment. A number of hydrogels have been developed for use as contact lenses. These hydrogels keep a layer of water at the surface of the eye to protect the eye from drying out.

The hydrogels used in coating the biosensors will typically be a polyurea, a polyurethane or a polyurethane/polyurea combination. FIG. 1 illustrates some of the polymerization reactions which result in the compositions of the present invention.

Hydrogel Components

The hydrogels which are used in the present invention are prepared from the reaction of a diisocyanate and a hydrophilic polymer, and optionally, a chain extender. The hydrogels are extremely hydrophilic and will have a water pickup of from about 120% to about 400% by weight, more preferably from about 150% to about 400%.

The diisocyanates which are useful in this aspect of the invention are those which are typically used in the preparation of biocompatible polyurethanes. Such diisocyanates are described in detail in Szycher, SEMINAR ON ADVANCES IN MEDICAL GRADE POLYURETHANES, Technomic Publishing, (1995) and include both aromatic and aliphatic diisocyanates (see FIGS. 2 and 3). Examples of suitable aromatic diisocyanates include toluene diisocyanate, 4,4'-diphenylmethane diisocyanate, 3,3'-dimethyl-4,4'-biphenyl diisocyanate, naphthalene diisocyanate and paraphenylene diisocyanate. Suitable aliphatic diisocyanates include, for example, 1,6-hexamethylene diisocyanate (HDI), trimethylhexamethylene diisocyanate (TMDI), trans-1,4-cyclohexane diisocyanate (CHDI), 1,4-cyclohexane bis(methylene isocyanate) (BDI), 1,3-cyclohexane bis(methylene isocyanate) ($H_6$XDI), isophorone diisocyanate (IPDI) and 4,4'-methylenebis(cyclohexyl isocyanate) ($H_{12}$MDI). In preferred embodiments, the diisocyanate is an aliphatic diisocyanate, more preferably isophorone diisocyanate, 1,6-hexamethylene diisocyanate, or 4,4'-methylenebis(cyclohexyl isocyanate). A number of these diisocyanates are available from commercial sources such as Aldrich Chemical Company (Milwaukee, Wis., USA) or can be readily prepared by standard synthetic methods using literature procedures.

The quantity of diisocyanate used in the reaction mixture for the present compositions is typically about 50 mol % relative to the combination of the remaining reactants. More particularly, the quantity of diisocyanate employed in the preparation of the present compositions will be sufficient to provide at least about 100% of the —NCO groups necessary to react with the hydroxyl or amino groups of the remaining reactants. For example, a polymer which is prepared using x moles of diisocyanate, will use a moles of a hydrophilic polymer (diol, diamine or combination), and b moles of a chain extender, such that x=a+b, with the understanding that b can be zero.

A second reactant used in the preparation of the swellable coatings described herein is a hydrophilic polymer. The hydrophilic polymer can be a hydrophilic diol, a hydrophilic diamine or a combination thereof. The hydrophilic diol can be a poly(alkylene)glycol, a polyester-based polyol, or a polycarbonate polyol (see FIG. 4). As used herein, the term "poly(alkylene)glycol" refers to polymers of lower alkylene glycols such as poly(ethylene)glycol, poly(propylene)glycol and polytetramethylene ether glycol (PTMEG). The term "polyester-based polyol" refers to a polymer as depicted in FIG. 4 in which the R group is a lower alkylene group such as ethylene, 1,3-propylene, 1,2-propylene, 1,4-butylene, 2,2-dimethyl-1,3-propylene, and the like. One of skill in the art will also understand that the diester portion of the polymer can also vary from the six-carbon diacid shown. For example, while FIG. 4 illustrates an adipic acid component, the present invention also contemplates the use of succinic acid esters, glutaric acid esters and the like. The term "polycarbonate polyol" refers those polymers having hydroxyl functionality at the chain termini and ether and carbonate functionality within the polymer chain (see FIG. 4). The alkyl portion of the polymer will typically be composed of C2 to C4 aliphatic radicals, or in some embodiments, longer chain aliphatic radicals, cycloaliphatic radicals or aromatic radicals. The term "hydrophilic diamines" refers to any of the above hydrophilic diols in which the terminal hydroxyl groups have been replaced by reactive amine groups or in which the terminal hydroxyl groups have been derivatized to produce an extended chain having terminal amine groups. For example, a preferred hydrophilic diamine is a "diamino poly(oxyalkylene)" which is poly(alkylene)glycol in which the terminal hydroxyl groups are replaced with amino groups. The term "diamino poly(oxyalkylene)" also refers to poly(alkylene) glycols which have aminoalkyl ether groups at the chain termini. One example of a suitable diamino poly (oxyalkylene) is poly(propylene glycol) bis(2-aminopropyl ether). A number of diamino poly(oxyalkylenes) are available having different average molecular weights and are sold as Jeffamines® (for example, Jeffamine 230, Jeffamine 600, Jeffamine 900 and Jeffamine 2000). These polymers can be obtained from Aldrich Chemical Company. Alternatively, literature methods can be employed for their synthesis.

The amount of hydrophilic polymer which is used in the present compositions will typically be about 10% to about 100% by mole relative to the diisocyanate which is used. Preferably, the amount is from about 50% to about 90% by mole relative to the diisocyanate. When amounts less than 100% of hydrophilic polymer are used, the remaining percentage (up to 100%) will be a chain extender.

Thus, in one group of embodiments, the reaction mixture for the preparation of swellable coatings will also contain a chain extender which is an aliphatic or aromatic diol, an aliphatic or aromatic diamine, alkanolamine, or combinations thereof (see FIG. 8). Examples of suitable aliphatic chain extenders include ethylene glycol, propylene glycol, 1,4-butanediol, 1,6-hexanediol, ethanolamine, ethylene diamine, butane diamine and 1,4-cyclohexanedimethanol. Aromatic chain extenders include, for example, para-di(2-hydroxyethoxy)benzene, meta-di(2-hydroxyethoxy) benzene, Ethacure 100® (a mixture of two isomers of 2,4-diamino-3,5-diethyltoluene), Ethacure 300® (2,4-diamino-3,5-di(methylthio)toluene), 3,3'-dichloro-4, 4'diaminodiphenylmethane, Polacure® 740 M (trimethylene glycol bis(para-aminobenzoate)ester), and methylenedianiline. Incorporation of one or more of the above chain extenders typically provides the resulting biocompatible membrane with additional physical strength, but does not substantially alter the hydrophilicity of the polymer. In particularly preferred compositions, the chain extender is butanediol, ethylenediamine, 1,6-hexamethylenediamine, 1,2-diaminocyclohexane or isophorone diamine. In one group of preferred embodiments, the chain extender is present an amount of from about 10% to 50% by mole relative to the diisocyanate.

Coating Preparation

Polymerization of the above reactants can be carried out in bulk or in a solvent system. Use of a catalyst is preferred, though not required. Suitable catalysts include dibutyltin bis(2-ethylhexanoate), dibutyltin diacetate, triethylamine and combinations thereof. Preferably dibutyltin bis(2-ethylhexanoate is used as the catalyst. Bulk polymerization is typically carried out at an initial temperature of about 25° C. (ambient temperature) to about 50° C., in order to insure adequate mixing of the reactants. Upon mixing of the reactants, an exotherm is typically observed, with the temperature rising to about 90°–120° C. After the initial exotherm, the reaction flask can be heated at from 75° C. to 125° C., with 90° C. to 100° C. being a preferred temperature range. Heating is usually carried out for one to two hours.

Solution polymerization can be carried out in a similar manner. Solvents which are suitable for solution polymerization include, tetrahydrofuran, dimethylformamide, dimethyl sulfoxide, dimethylacetamide, halogenated solvents such as 1,2,3-trichloropropane, and ketones such as 4-methyl-2-pentanone. Preferably, THF is used as the solvent. When polymerization is carried out in a solvent, heating of the reaction mixture is typically carried out for at least three to four hours, and preferably at least 10–20 hours.

At the end of this time period, the solution polymer is typically cooled to room temperature and poured into DI water. The precipitated polymer is collected, dried, washed with hot DI water to remove solvent and unreacted monomers, then re-dried. The dried polymer can be evaluated for water pickup as described in the Examples below.

The hydrogels which are useful in the present invention will have a water pickup of at least 120%, preferably 150% to about 400%, and more preferably about 200% to about 400%.

Polymers prepared by bulk polymerization are typically dissolved in dimethylformamide and precipitated from water. Polymers prepared in solvents such as THF can be poured into water at ambient temperatures, then filtered, dried, washed with boiling water and re-dried.

Once the polymers have been prepared having suitable water pickup, the polymers can be solubilized in a solvent and used to coat a biosensor.

Preparation of coated biosensors can be accomplished by dissolving the dried polymer in a suitable solvent and spin-coating the sensor, typically using, for example, a 5 wt % in 2-propanol solution of the polymer. The selection of other suitable solvents for coating the sensors will typically depend on the particular polymer as well as the volatility of the solvent. Other suitable solvents include THF, $CHCl_3$, $CH_2Cl_2$, DMF or combinations thereof. More preferably, the solvent is THF or $DMF/CH_2Cl_2$ (2/98 volume %).

A number of different sensors can be used in the methods and compositions of the present invention.

Membrane-Coated Biosensors

Glucose sensors which utilize, for example, glucose oxidase to effect a reaction of glucose and oxygen are known in the art, and are within the skill in the art to fabricate. See, for example, U.S. Pat. Nos. 5,165,407, 4,890,620, 5,390,671 and 5,391,250, the disclosures of each being incorporated herein by reference. The present invention depends not on the configuration of the biosensor, but rather on the use of the inventive membranes to cover or encapsulate the sensor elements.

In particular, the hydrogels described herein are particularly useful with a variety of biosensors for which it is advantageous to provide a surrounding water layer for the electrodes. Various such biosensors are well known in the art. For example, sensors for monitoring glucose concentration of diabetics are described in Shichiri, et al.,: "In Vivo Characteristics of Needle-Type Glucose Sensor-Measurements of Subcutaneous Glucose Concentrations in Human Volunteers," *Horm. Metab. Res., Suppl. Ser.* 20:17-20 (1988); Bruckel, et al.,: "In Vivo Measurement of Subcutaneous Glucose Concentrations with an Enzymatic Glucose Sensor and a Wick Method," *Klin. Wochenschr.* 67:491-495 (1989); and Pickup, et al.,: "In Vivo Molecular Sensing in Diabetes Mellitus: An Implantable Glucose Sensor with Direct Electron Transfer," *Diabetologia* 32:213-217 (1989).

Other sensors are described in, for example Reach, et al., in ADVANCES IN BIOSENSORS, A. Turner (ed.), JAI Press, London, Chap. 1, (1993), incorporated herein by reference.

The following examples are offered by way of illustration and are not meant to limit the scope of the invention.

EXAMPLES

The materials used in the examples were obtained from the following sources: isophorone diisocyanate, 1,6-hexamethylenediisocyanate, PEG 600, butanediol, ethylene diamine, hexamethylenediamine, isophorone diamine and 1,2-diaminohexane (Aldrich Chemical Co., Milwaukee, Wis., USA); Jeffamine® D-230, ED-600, ED-900 and D-2000 were obtained from Aldrich.

General Methods (a) Hydrogel Preparation

Hydrogels suitable for use as biosensor coatings were prepared by combining a diisocyanate with an equivalent molar amount of a hydrophilic diol or diamine or with a combination of diol or diamine and chain extender such that the molar amount of the combination was equivalent to the diisocyanate. The polymerizations were carried out in a one-pot reaction using THF as solvent and a trace catalyst (tributyltin ethylhexanoate). The reactions were heated to reflux and held at this temperature overnight (about 16 hours). The resulting polymer solution was poured into a large volume of DI water at about 20° C. and then filtered, dried, and washed with boiling DI water. The resulting polymer was again dried then taken up in 2-propanol (as a 5 wt % solution) and used for spin coating.

(b) Coating of Biosensors

Coating of biosensors can be carried out using a commercial spin coating apparatus operating at between 1000 and 5000 rpm, depending on the viscosity of the polymer solution and the desired thickness of the hydrophilic coating.

(c) Water Pickup

Water pickup was determined gravimetrically at room temperature on polymers which had been dried to a constant weight at 50° C. in vacuo, then weighed, immersed in deionized water for 24 hours, removed and blotted with filter paper, and weighed. Percent water pickup was determined from the formula:

$$\% \text{ Pickup} = (W_w - W_d)/W_d \times 100$$

where $W_w$ is the weight of the swollen film and $W_d$ is the weight of the dry film.

(d) Impedance Measurements

Electrochemical impedance measurements were performed on finished sensors using a Bioanalytical Systems (BAS, Lafayette, Ind.) 100B Electrochemical Analyzer. Impedance was measured in a three electrode mode from 0.01 Hz to 1000 Hz. Linear extrapolation to DC impedance was used to obtain the final impedance figures. The final impedance is calculated as the sum of the real and imaginary parts of the impedance. The measurements were made in 100 mg/dl glucose solution in PBS, with a 600 mv applied potential and a 5 mv A.C. signal imposed on the applied potential.

Example 1

This example provides the formulations and properties of representative coatings.

Table 1 provides ten formulations for representative polymers which were prepared by solution polymerization.

TABLE 1

| Representative Polymer Formulations | | | |
|---|---|---|---|
| Polymer | Diisocyanate | Hydrophilic diol or diamine | Chain Extender |
| 1 | 1,6-Hexamethylene | Jeffamine 600 (95%) | Butanediol (5%) |
| 2 | 1,6-Hexamethylene | Jeffamine 2000 (100%) | None |

TABLE 1-continued

| Representative Polymer Formulations | | | |
|---|---|---|---|
| Polymer | Diisocyanate | Hydrophilic diol or diamine | Chain Extender |
| 3 | 1,6-Hexamethylene | Jeffamine 2000 (90%) | Butanediol (10%) |
| 4 | 1,6-Hexamethylene | PEG 2000 (90%) | Butanediol (10%) |
| 5 | 1,6-Hexamethylene | Jeffamine 230 (30%) | Ethylene diamine (70%) |
| 6 | 1,6-Hexamethylene | PEG 600 (75%) | Ethylene diamine (25%) |
| 7 | Isophorone | PEG 600 (75%) | Butanediol (25%) |
| 8 | Isophorone | Jeffamine 900 (70%) | 1,6-Diaminohexane (25%) |
| 9 | Isophorone | Jeffamine 900 (50%) | 1,2-Diaminocyclohexane (50%) |
| 10 | Isophorone | Jeffamine 900 (50%) | Isophorone diamine (50%) |

Table 2 provides certain physical and chemical properties of the polymers above.

TABLE 2

| Physical Properties of Representative Polymers | | |
|---|---|---|
| Polymer | Water Pickup (%) | Impedance (Ohms) ($\times 10^6$) |
| 1 | 250 | 2.3 |
| 2 | 160 | 1.7 |
| 3 | 240 | 1.4 |
| 4 | 400 | 6.1 |
| 5 | 110 | 3.3 |
| 6 | 45 | 6.9 |
| 7 | 280 | 1.1 |
| 8 | 240 | 0.7 |
| 9 | 220 | 0.5 |
| 10 | 184 | 0.8 |

Example 2

This example illustrates the evaluation of a membrane-coated biosensor constructed according to the present invention.

Figure 6B:
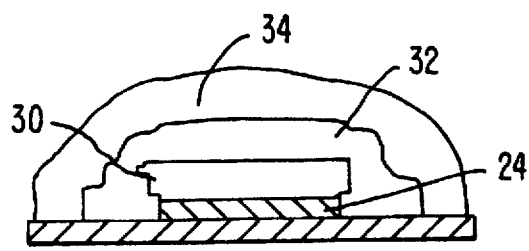
FIG. 6B is a sectional side view of a working electrode of the sensor which is covered with layers of an enzyme, a glucose-limiting polymer and a hydrogel composition of the invention.

A membrane prepared from the polymer identified as 9 above was found to have excellent mechanical properties as well as appropriate water uptake and oxygen and glucose diffusivities. The membrane was evaluated using a prototype glucose sensor illustrated in FIG. 6A. According to FIG. 6A, a sensor 20 was constructed having a reference electrode 22, a working electrode 24, and a counter electrode 26 deposited on a polymeric sheet 29. A series of bonding pads 28 complete the sensor 20. As shown in FIG. 6B, the working electrode 24 was covered with a layer 30 of the enzyme glucose oxidase and the entire electrode array was coated with a first layer 32 of a glucose-limiting polymer prepared according to U.S. Ser. No. 08/721,262 (Attorney Docket No. 017898-000410, filed Sep. 26, 1996 and incorporated herein by reference) and a second layer 34 of the polymer 9 (see Example 1) by spin coating. The glucose limiting polymer was applied from a 7 wt % solution of the polymer in THF and the hydrophilic coating 34 was applied from a 5 wt % solution in 2-propanol. The sensor was connected to a commercial potentiostat (BAS Instruments, not shown) and operated with a potential of +0.6 volts between the working electrode and the reference electrode.

The above description is illustrative and not restrictive. Many variations of the invention will become apparent to those of skill in the art upon review of this disclosure. Merely by way of example a variety of solvents, membrane formation methods, and other materials may be used without departing from the scope of the invention. The scope of the invention should, therefore, be determined not with reference to the above description, but instead should be determined with reference to the appended claims along with their full scope of equivalents.

All publications, patents and patent applications mentioned in this specification are herein incorporated by reference into the specification to the same extent as if each individual publication, patent or patent application was specifically and individually indicated to be incorporated herein by reference.

What is claimed is:

1. A method of reducing electrode impedance of an implantable biosensor comprising coating said biosensor with a hydrogel, wherein said hydrogel is formed from a reaction mixture of:
   (a) a diisocyanate, said diisocyanate comprising about 50 mol % of the reactants in said mixture;
   (b) a hydrophilic polymer which is a member selected from the group consisting of a hydrophilic polymer diol, a hydrophilic polymer diamine and combinations thereof; and optionally;
   (c) a chain extender, said hydrogel having a water pickup of from about 120% to about 400% by weight.

2. A method in accordance with claim 1, wherein said coating is by spin coating, dipping or spraying.

3. A method in accordance with claim 1, wherein said hydrophilic polymer is a poly(ethylene)glycol selected from the group consisting of PEG 600, PEG 2000, Jeffamine D-230, Jeffamine ED-600, Jeffamine ED-900 and Jeffamine D-2000.

4. A method in accordance with claim 1, wherein said diisocyanate is a member selected from the group consisting of isophorone diisocyanate, 1,6-hexamethylene diisocyanate and 4,4'-methylenebis(cyclohexyl isocyanate).

5. A method in accordance with claim 1, wherein said chain extender is selected from the group consisting of an alkylene diol, an alkylene diamine, an aminoalkanol and combinations thereof.

6. A method in accordance with claim 1, wherein said chain extender is selected from the group consisting of butanediol, ethylenediamine, hexamethylenediamine, 1,2-diaminocyclohexane and isophoronediamine.

7. A method in accordance with claim 1, wherein said diisocyanate is 1,6-hexamethylene diisocyanate and said hydrophilic polymer is selected from the group consisting of Jeffamine ED-600, Jeffamine D-2000 and PEG 2000 and is present in an amount of about 40 to about 50 mol %.

8. A method in accordance with claim 1, wherein said diisocyanate is 1,6-hexamethylene diisocyanate, said hydrophilic polymer is selected from the group consisting of Jeffamine ED-600, Jeffamine D-2000 and PEG 2000 and is present in an amount of about 40 to about 50 mol % and said chain extender is butanediol and is present in an amount of about 2.5 to about 10 mol %.

9. An implantable biosensor having a hydrogel coating, said coating prepared from a reaction mixture of:
   (a) a diisocyanate, said diisocyanate comprising about 50 mol % of the reactants in said mixture;
   (b) a hydrophilic polymer which is a member selected from the group consisting of a hydrophilic polymer diol, a hydrophilic polymer diamine and combinations thereof; and optionally;
   (c) a chain extender; wherein said coating has a water pickup of from about 120% to about 400% by weight.

10. An implantable biosensor in accordance with claim 9, wherein said hydrophilic polymer is a poly(ethylene)glycol selected from the group consisting of PEG 600, PEG 2000, Jeffamine D-230, Jeffamine ED-600, Jeffamine ED-900 and Jeffamine D-2000.

11. An implantable biosensor in accordance with claim 9, wherein said diisocyanate is a member selected from the group consisting of isophorone diisocyanate, 1,6-hexamethylene diisocyanate and 4,4'-methylenebis (cyclohexyl isocyanate).

12. An implantable biosensor in accordance with claim 9, wherein said chain extender is selected from the group consisting of an alkylene diol, an alkylene diamine, an aminoalkanol and combinations thereof.

13. An implantable biosensor in accordance with claim 9, wherein said chain extender is selected from the group consisting of butanediol, ethylenediamine, hexamethylenediamine, 1,2-diaminocyclohexane and isophoronediamine.

14. An implantable biosensor in accordance with claim 9, wherein said diisocyanate is 1,6-hexamethylene diisocyanate and said hydrophilic polymer is selected from the group consisting of Jeffamine ED-600, Jeffamine D-2000 and PEG 2000 and is present in an amount of about 40 to about 50 mol %.

15. An implantable biosensor in accordance with claim 9, wherein said diisocyanate is 1,6-hexamethylene diisocyanate, said hydrophilic polymer is selected from the group consisting of Jeffamine ED-600, Jeffamine D-2000 and PEG 2000 and is present in an amount of about 40 to about 50 mol % and said chain extender is butanediol and is present in an amount of about 2.5 to about 10 mol %.

* * * * *